(12) United States Patent
El Ichi et al.

(10) Patent No.: US 10,316,284 B2
(45) Date of Patent: Jun. 11, 2019

(54) IMPLANTABLE BIOCOMPATIBLE REACTOR

(71) Applicant: UNIVERSITE GRENOBLE ALPES, Saint Martin d'Heres (FR)

(72) Inventors: Sarra El Ichi, La Tronche (FR); Donald K. Martin, La Tronche (FR); Philippe Cinquin, La Tronche (FR); Abdelkader Zebda, La Tronche (FR)

(73) Assignee: Universite Grenoble Alpes, Saint Martin d'Heres (FR)

( * ) Notice: Subject to any disclaimer, the term of this patent is extended or adjusted under 35 U.S.C. 154(b) by 45 days.

(21) Appl. No.: 15/126,236

(22) PCT Filed: Mar. 23, 2015

(86) PCT No.: PCT/FR2015/050725
§ 371 (c)(1),
(2) Date: Sep. 14, 2016

(87) PCT Pub. No.: WO2015/145054
PCT Pub. Date: Oct. 1, 2015

(65) Prior Publication Data
US 2017/0081626 A1    Mar. 23, 2017

(30) Foreign Application Priority Data

Mar. 25, 2014 (FR) ...................... 14 52534

(51) Int. Cl.
| | | |
|---|---|---|
| C12M 1/00 | (2006.01) |
| H01M 4/86 | (2006.01) |
| H01M 4/88 | (2006.01) |
| H01M 4/90 | (2006.01) |
| H01M 8/16 | (2006.01) |
| B29C 41/00 | (2006.01) |
| B29C 65/48 | (2006.01) |
| G01N 27/327 | (2006.01) |
| B29L 31/00 | (2006.01) |
| B29L 31/34 | (2006.01) |

(52) U.S. Cl.
CPC ........... *C12M 29/04* (2013.01); *B29C 41/003* (2013.01); *B29C 65/4805* (2013.01); *G01N 27/3271* (2013.01); *H01M 4/8605* (2013.01); *H01M 4/8663* (2013.01); *H01M 4/8673* (2013.01); *H01M 4/8896* (2013.01); *H01M 4/9008* (2013.01); *H01M 4/9083* (2013.01); *H01M 8/16* (2013.01); *B29K 2005/00* (2013.01); *B29K 2995/0068* (2013.01); *B29L 2031/34* (2013.01); *B29L 2031/755* (2013.01); *H01M 2250/30* (2013.01); *Y02B 90/18* (2013.01); *Y02E 60/527* (2013.01)

(58) Field of Classification Search
None
See application file for complete search history.

(56) References Cited

U.S. PATENT DOCUMENTS

| | | | | |
|---|---|---|---|---|
| 4,918,016 | A * | 4/1990 | Leuba .................. | A23C 9/1206 435/176 |
| 9,708,640 | B2 * | 7/2017 | Wu ......................... | C12Q 1/54 |
| 2011/0039164 | A1 | 2/2011 | Akers et al. | |
| 2011/0250510 | A1 | 10/2011 | Cinquin et al. | |
| 2013/0284596 | A1 | 10/2013 | Zebda et al. | |
| 2014/0322617 | A1 | 10/2014 | Wang et al. | |
| 2016/0296665 | A1 * | 10/2016 | Ingber ..................... | C08L 5/08 |

FOREIGN PATENT DOCUMENTS

| | | |
|---|---|---|
| EP | 2375481 | 10/2011 |
| FR | 2958801 A1 | 10/2011 |
| FR | 2963989 A1 | 2/2012 |
| WO | 2013130145 A2 | 9/2013 |

OTHER PUBLICATIONS

Holzinger Michael et al: "Carbon nanotubelenzyme biofuel cells", Electrochimica Acta, vol. 82, Mar. 3, 2012, pp. 179-190.
International Searching Authority, Written Opinion, PCT/FR2015/050725, dated Mar. 23, 2015, English Translation.

\* cited by examiner

*Primary Examiner* — Blaine Lankford
(74) *Attorney, Agent, or Firm* — Kevin R. Erdman; Brannon Sowers & Cracraft PC

(57) ABSTRACT

The invention concerns a bioreactor obtained by compressing a mixture of an enzyme, a conductor and chitosan. The conductor can consist of carbon nanotubes. This bioreactor can be produced according to the following steps: preparing a mixture of powders in which the proportion of enzyme powder relative to a carbon nanotube powder is of the order of 50/50 by weight; preparing a viscous solution of chitosan in a ratio of 5 to 15 (in mg) of chitosan to 0.75 to 1.25 (in ml) of acetic acid diluted to 0.4 to 0.6% by volume in water; adding the viscous chitosan to the mixture of powders in a proportion be weight of 3 to 5 of powder to 5 to 10 of chitosan; carrying out a first compression followed by light grinding; carrying out a second compression to produce a pellet; and drying at ambient temperature.

13 Claims, 2 Drawing Sheets

IMPLANTABLE BIOCOMPATIBLE REACTOR

CROSS-REFERENCE TO RELATED APPLICATIONS

The present application is a National Stage of PCT International Application Ser. No. PCT/FR2015/050725, filed Mar. 23, 2015, and claims priority under 35 U.S.C. § 119 of France, Patent Application Serial Number 14/52,534, filed Mar. 25, 2014, the disclosures of which are incorporated by reference herein.

BACKGROUND

The present invention relates to a reactor implantable in vivo, where a reaction is capable of occurring between elements confined in the reactor and compounds present in the host organism. The reaction may for example result in a deformation of the reactor, in the generation of an electric potential, or in the chemical transformation of the compound interacting with the reactor.

A reactor causing the generation of an electric potential may form an electrode of a biofuel cell or of a biosensor, of sugar-oxygen type, for example, glucose-oxygen.

A reactor causing the chemical transformation of a compound interacting with the reactor will for example form a glucose killer by, for example, transforming glucose into a compound which will be eliminated by the organism.

Although the invention and the state of the art are described herein mainly in the case of bioelectrodes of a biofuel cell, it should be understood that the invention generally applies to any reactor implantable in vivo.

DISCUSSION OF RELATED ART

Various types of glucose-oxygen biofuel cells are described in prior art, for example, in patent application PCT/PR2009/050639 (B8606), in such known biofuel cells, each electrode, anode and cathode, corresponds to an enclosure containing a liquid medium having an electrode wire plunged therein. The anode and cathode enclosures are delimited by membranes capable of being crossed by hydrogen and oxygen but avoiding the circulation of other heavier elements.

The anode comprises in a solution an enzyme and a redox mediator. The enzyme is capable of catalyzing the oxidation of sugar and is for example selected from the group comprising glucose-oxidase if the sugar is glucose and lactase-oxidase if the sugar is lactose. The redox mediator has a low redox potential capable of exchanging electrons with the anode enzyme and is for example selected from the group comprising: ubiquinone (UQ) and ferrocene.

The cathode also comprises, in a solution, an enzyme and preferably a redox mediator. The enzyme is capable of catalyzing the reduction of oxygen and is for example selected from the group comprising: polyphenol oxidase (PPO), laccase, and bilirubin oxidase. The redox mediator has a high redox potential capable of exchanging electrons with the cathode enzyme and is for example selected from the group comprising: hydroquinone (QH2) et 2,2'-azinobis-(3-ethylbenzo-thiazolin-6-sulfonate) (ABTS).

Reactions of the following type then occur at the anode and at the cathode:

Cathode:

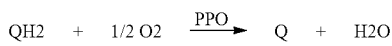

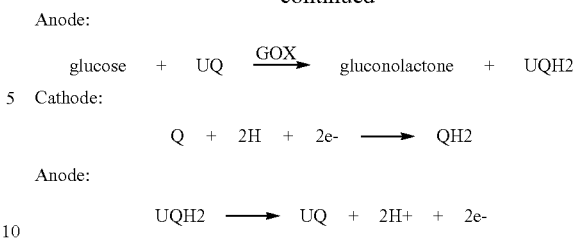

the reactions being given in the specific case where the sugar is glucose, the anode enzyme is glucose-oxidase (GOX), the anode redox mediator is ubiquinone (UQ), the cathode enzyme is polyphenol oxidase (PPO), and the cathode redox mediator is quinhydrone (QH2). A 20-mV anode potential and a 250-mV cathode potential are then obtained, which results in a 230-mV zero-current potential difference of the biofuel cell.

Such biofuel cells operate properly but, especially as concerns the biofuel cell described in patent application PCT/FR2009/050639, they require for the anode and cathode conductors to be plunged in enclosures containing suitable liquids, which is a practical disadvantage in many cases and makes it in particular very difficult, or even impossible, to implant such biofuel cells in a living being.

Indeed, such biofuel cells are attempted to be implanted in living beings, especially to power various actuators, such as heart stimulators, artificial sphineters, or even artificial hearts.

Biofuel cells with solid electrodes have been provided. However, biofuel cells using such electrodes, especially when they are implanted in a living being, have a very short lifetime.

A glucose oxygen biofuel cell implantable in vivo is described, in particular, in European patent EP 2375481 of the applicant (B10272). The content of this patent will be incorporated herein by reference.

In this patent, it is provided to manufacture biofuel cell anode and cathode pellets from a compression of a conductor such as graphite and an enzyme having a redox mediator added thereto. The cathode and the anode, as well as, preferably, the assembly of the anode and the cathode, are surrounded with a semi-permeable enclosure, for example, of the type used in dialysis, to give way to glucose and oxygen and block enzymes and redox mediators. The conductive material from which the anode compression and the cathode compression are performed is indicated as being graphite or a conductive polymer.

FIG. 1 hereafter is a copy of FIG. 2 of this prior patent it shows an anode pellet A and a cathode pellet K respectively attached to conductors 1 and 3. The anode is surrounded with a semi-permeable membrane 11, the cathode is surrounded with a semi-permeable membrane 12, and the assembly is surrounded with a semi-permeable membrane 13.

Satisfactory in vivo experimental results have been obtained with the biofuels cell electrodes described in this patent.

It is however desirable to further improve the electrode lifetime, that is, the operating duration of the biofuel cell, and to improve the biocompatibility of the cell as much as possible.

More generally, it is desirable to further improve the lifetime of bioreactors such as defined hereabove.

SUMMARY

Thus, a bioreactor obtained by compression of a mixture of an enzyme, of a conductor, and of chitosan is provided herein.

According to an embodiment, the conductor is formed of carbon nanotubes.

A method of manufacturing a bioreactor is also provided, comprising the steps of:

eparing a mixture of powder where the proportion of enzyme powder relative to a carbon nanotube powder is of the order of 50/50 by weight;

preparing a viscous solution of chitosan in a ratio of 5 to 15 (in mg) of chitosan to 0.75 to 1.25 (in ml) of acetic acid diluted to 0.4 to 0.6% by volume in water;

adding the viscous chitosan to the mixture of powders in a proportion by weight of 3 to 5 for the powder to 5 to 10 of chitosan;

carrying out a first compression followed by light grinding;

carrying out a second compression to produce a pellet; and drying at ambient temperature;

According to an embodiment, the pressure applied during the first and the second compression is within a range from 2,000 to 6,000 kPa.

According to an embodiment, the solution comprises from 0.002 to 0.005% in mass per volume of genipin.

According to an embodiment, the solution comprises from 0.001 to 0.005% in mass per volume of caffeic acid.

A bioreactor is also provided, wherein a porous chitosan-based membrane is laid on the active surface and bonded at the periphery thereof.

According to an embodiment, the bioreactor forms a pellet-shaped bioelectrode, where the conductor is glued by means of conductive glue to the surface of the pellet opposite to the active surface.

According to an embodiment, the membrane comprises pores having an average diameter in the range from 1 to 10 nanometers.

According to an embodiment, the membrane comprises a smooth surface facing the pellet and a rough surface facing outwards.

A method of manufacturing a porous membrane for a bio-reactor is also provided, comprising the steps of:

preparing a solution in a ratio of 5 to 15 (in mg) of chitosan to 0.75 to 1.25 (in ml) of acetic acid diluted to 0.4 to 0.6% in water;

stirring;

passing on a smooth support; and drying for a period from 2 to 4 days at ambient temperature.

BRIEF DESCRIPTION OF THE DRAWINGS

The foregoing and other features and advantages will be discussed in detail in the following non-limiting description of specific embodiments in connection with the accompanying drawings, among which.

DETAILED DESCRIPTION

Figure 1:
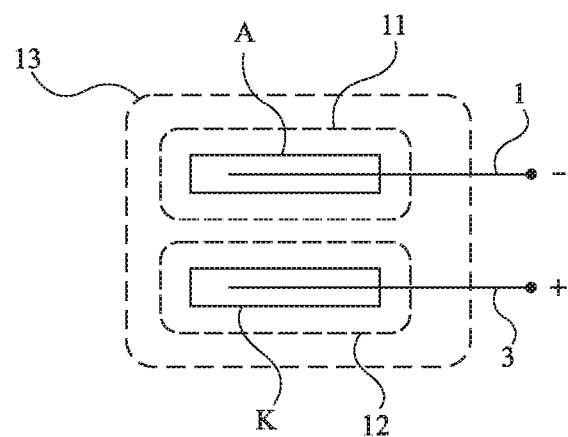
FIG. 1 corresponds to FIG. 2 of European patent EP 2375481.

If is here first provided to manufacture a bioelectrode pellet from a compression of chitosan, of an enzyme, and of a conductor, and possibly of a redox mediator and other additives, rather than from the compression of only one conductor and one enzyme. The conductor may advantageously be formed of multiwalled carbon nanotubes (MW-CNT).

A mixture of powders of an enzyme and of carbon nano-tubes, the proportion of enzyme powder relative to the carbon nanotube powder being in the order of 50/50 by weight, this proportion being likely to vary by approximately 20%.

A viscous solution of chitosan is also prepared by adding chitosan powder in acetic acid diluted to 0.5% by volume heated up to 50° C., and by stirring for 2 hours at ambient temperature.

The viscous chitosan is added to the powder mixture in a proportion by weight of 2 for the powder to 3 for the chitosan. For a chitosan pellet, 0.04 gram of powder and 0.06 gram of chitosan will for example be used.

A mixture of the powder and of the chitosan in the viscous state is formed and a first compression, followed by a light grinding, is performed. A second compression which, like the first compression, is carried out at a pressure selected within a range from 2,000 to 6,000 kPa is then performed to provide a pellet, after which a drying is performed for from two to four days at ambient temperature (from 20 to 30° C.) so that the assembly can polymerize.

A crosslinking agent for example, genipin at 0.0045% in mass per volume (g/100 ml) in the viscous chitosan solution alter 2 hrs of stirring. The genipin is previously solubilized in a solution of 12% of dimethylsulfoxide (DMSO) and 88% of water (H2O). To improve the resistance of the membrane to acids, a product such as caffeic acid by a proportion of 0.0032% in mass per volume (g/100 ml) in the viscous chitosan solution may be added to the initial mixture. The caffeic acid is previously solubilized to 4% in ethanol. The solution is stirred for 30 min before sampling 3 g to be spread on the smooth support for the drying, as previously described.

A characteristic of the method described herein is that, during the second compression and the diving, the chitosan takes the form of long interconnected fibers having an approximate 30-nm diameter. It should be noted that a nanofiber and nanopore three-dimensional array is obtained simply by compression of the polymer with the powder and evaporation of the solvent at ambient temperature. As a result, the enzyme and the carbon nanotubes are immobilized in the chitosan fiber matrix and do not migrate to the outside of the pellet. This provides a significant advantage since the enzyme, which is trapped by the fiber matrix, remains protected and active for a long time. Further, the carbon nanotubes should be trapped, questions actually arising as to the possible noxiousness of carbon nanotubes in vivo.

A biocathode comprising only one conductor and one enzyme, such as described in prior above-mentioned patent, has a 1-month stability in intermittent operation. A biocathode based on chitosan-MWCNT-laccase, such as described herein, has a stability greater than 2 months in continuous operation. In vitro measurements show that the stability in intermittent operation of the biocathode described herein exceeds six months. Further, such a stability is also ensured in vivo for a period longer than 200 days. This shows that the bioelectrode described herein provides the enzyme with an environment protecting the activity thereof, but also retains the enzyme within the electrode pellet and close to the carbon nanotubes for electric conduction. The porosity of the three-dimensional chitosan matrix allows a good diffusion of the enzyme substrates.

As a variation, graphene, gold powder, or a conductive polymer such as polyaniline may be used as a conductor instead of using carbon nanotubes.

Specific embodiments have teen described. Various alterations and modifications will occur to those skilled in the art. In particular, the polymer may be chitosan or another biocompatible polymer, for example: polyvinyl alcohol, poly(methylmethacrylate), gelatin, dextran, or copolymers such as chitosan-polyethylene glycol, or a mixture of these polymers.

The method of manufacturing the electrodes based on conductive polymer and enzyme may be applied to the cathode or to the anode. Different enzymes may be immobilized in this structure: laccase, bilirubin-oxidase, polyphenol-oxidase, glucose-oxidase, glucose-deshydrogenase, catalase, peroxidase.

According to another aspect of the present invention, a specific filtering membrane is provided for an enzyme bioelectrode such as hereabove or any other enzyme bioelectrode obtained by compression of a conductor, of an enzyme, and possibly of a redox mediator—the redox mediator being optional in the cathode.

Figure 2A:
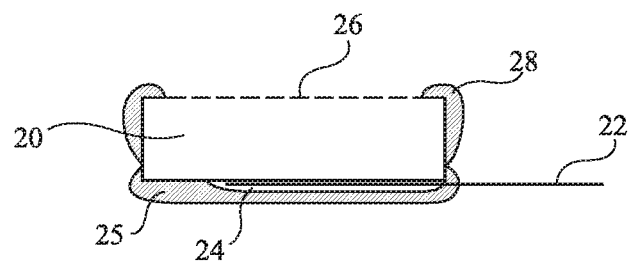
FIGS. 2A and 2B respectively are a cross-section view and a top view of an embodiment of an electrode.
Figure 2B:
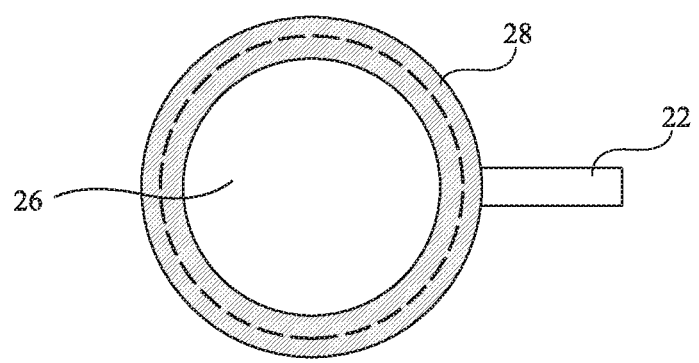

As illustrated in FIGS. 2A and 2B, the electrode appears in the form of a pellet 20 for example having a circular shape in top view, a diameter from 0.5 to 1 cm, and a thickness from 0.5 to 2 mm. The lower surface of pellet 20 has a conductive strip 22 bonded thereto, for example, by conductive glue, for example a carbon paste 24, itself coated with a protective silicone glue layer 25, selected from among biocompatible glues. On the upper surface of pellet 20 is laid—not deposited—a membrane 26 glued at its periphery to the pellet by a silicone glue ring 28.

It is here provided to use a chitosan-based membrane for membrane 26. This membrane is for example obtained by starting from a solution in a ratio from 5 to 15, for example, 10 (mg) of chitosan to 0.75 to 1.25, for example, 1 (in ml) of acetic acid diluted to 0.4 to 0.6% by volume in water and heated up to 50° C. In a test, a dissolution of 200 mg of chitosan in 20 ml of acetic acid diluted to 0.5% by volume in water has been carried out. The mixture is stirred for two hours. 3 g of this mixture have then been sampled and spread on a non-adhesive smooth support (28-cm diameter), for example, an antistatic polystyrene cup, and dried for from 2 to 4 days at ambient temperature, for example, at a temperature from 20 to 30° C. In a test, the drying has been carried out for three days at 25° C.

A flexible nanoporous film is thus obtained. Experiments carried out by the applicant have shown that this flexibility is due to the fact that the drying is carried out for a long time at ambient temperature. This characteristic is not obtained, for example, if drying temperatures greater than 40° C. ate used. For a film thickness in the range from 7 to 15 μm, for example, 10 μm, a porous membrane having average porous diameters in the range from 1 to 10 nanometers has been obtained. Conditions where this average diameter is in the range from 5 to 8 nm will be preferred to give way to glucose and to filter the compounds having the largest dimensions.

In the same way as in the context of the forming of a pellet, a crosslinking agent, for example, genipin, and an agent of resistance to acids, for example, caffeic acids, may be added to the initial mixture.

The obtained film exhibits a surface roughness difference between the two surfaces, which is due to the fact that one of the surfaces (the roughest) has been in contact with air rather than with the support (smooth surface). During the assembly, the rough surface will preferably be placed with its rough surface facing outwards with respect to the surface of the bioelectrode pellet. Indeed, the roughness difference on a thin film influences the ion diffusion and accordingly the electric resistivity. The inventors have shown that the chitosan film has a good ion conductivity (10-4 S.cm-1). Such an ion conductivity is better than that obtained with commercial membranes such as Nafion or cellulose acetate.

The chitosan film described herein enables, by its mechanical properties, and particularly its flexibility and its adequate swelling ratio, to provide mechanical stability to the electrode by taking the shape of the surface of the pellet after swelling thereof in the liquid. It provides a biocompatible interface in contact with the tissues after implantation of the biofuel cell. It forms an efficient barrier against a possible salting out of the electrode components, oh the one hand, and against biological molecules originating from the extracellular fluid.

The pore diameter may be adjusted by modifying: the chitosan concentration in the solvent (acetic acid), the chitosan/crosslinking agent ratio, the molecular weight of the powder chitosan placed in the initial acetic acid solution.

Figure 3:
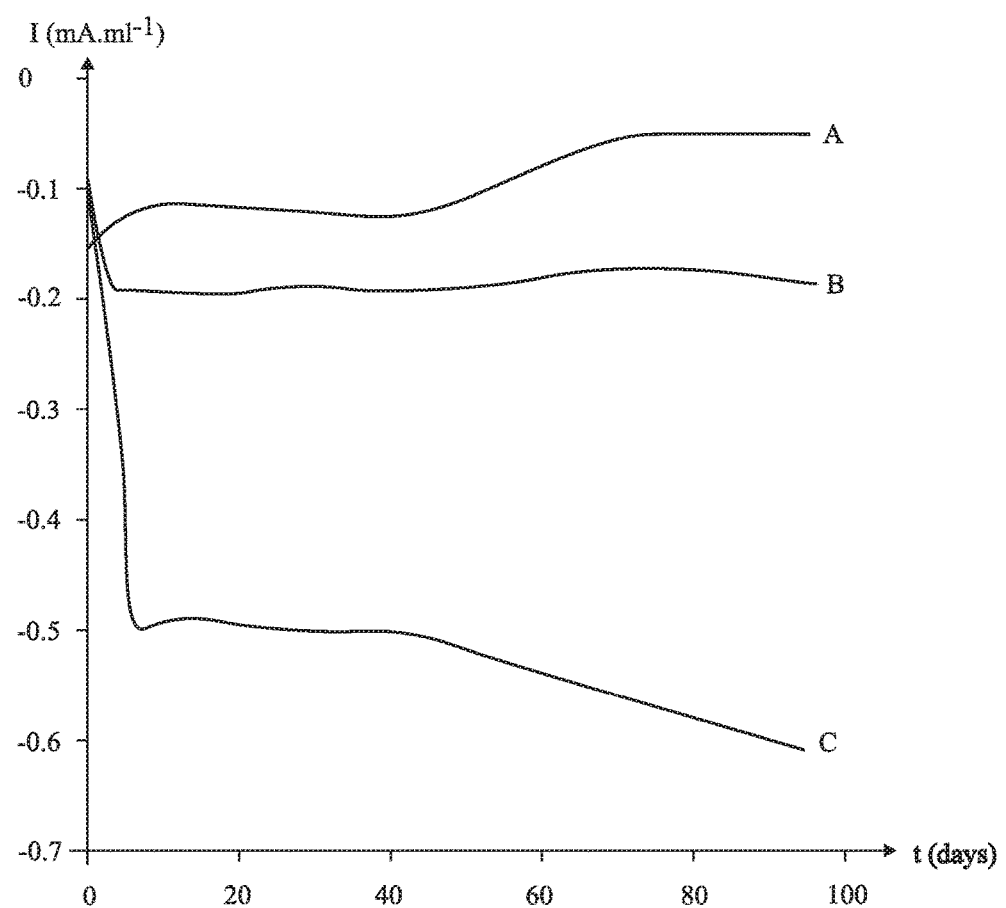
FIG. 3 shows current-vs.-time characteristics of various biofuels cells.

FIG. 3 shows a characteristic in mA/ml (milliliters corresponding to the pellet volume) of current versus time in days for various biofuels cells. Curve A corresponds to the case where a cellulose acetate membrane has been used, curve B corresponds to the case a Nafion membrane has been used, and curve C corresponds to the cases where a chitosan-based membrane such as previously described has been used. It can be observed that the (negative) current is much greater in the case of the chitosan-based membrane and that the characteristics of the biofuels cell are actually not altered along time. It should further be noted that for cellulose acetate, the characteristic starts from a value of −0.15 and falls to a value in the order of −0.05 after approximately 70 days. With a Nafion membrane, a relatively constant characteristic is obtained, with current densities from two to three times smaller than with a chitosan-based membrane.

Although the invention and the state of the art are described herein mainly in the case of a bioelectrode, it should be understood that the invention generally applies to any bioreactor implantable in vivo, such as defined at the beginning of the present description.

The invention claimed is:

1. A bioreactor obtained by a method comprising the steps of:
   preparing a mixture of an enzyme powder and a carbon nanotube powder where the proportion of enzyme powder relative to carbon nanotube powder is of the order of 50/50 by weight;
   preparing a viscous solution of chitosan in a ratio of 5 to 15 (in mg) of chitosan to 0.75 to 1.25 (in ml) of acetic acid diluted to 0.4 to 0.6% by volume in water;
   adding the viscous chitosan to the mixture of enzyme powder and carbon nanotube powder in a proportion by weight of 3 to 5 of this mixture to 5 to 10 of chitosan;
   carrying out a first compression followed by light grinding;
   carrying out a second compression to produce a pellet; and
   drying at ambient temperature.

2. The bioreactor of claim 1, wherein the pressure applied during the first and the second compression is within a range from 2,000 to 6,000 kPa.

3. The bioreactor of claim 1, wherein the solution comprises from 0.002 to 0.005% in mass per volume of genipin.

4. The bioreactor of claim 1, wherein the solution comprises from 0.001 to 0.005% in mass per volume of caffeic acid.

5. The bioreactor of claim 1, wherein a porous chitosan-based membrane is laid on an active surface of the bioreactor and bonded at the periphery thereof.

6. The bioreactor of claim 5, wherein the porous chitosan-based membrane is obtained by a method comprising the steps of:
   preparing a solution in a ratio of 5 to 15 (in mg) of chitosan to 0.75 to 1.25 (in ml) of acetic acid diluted to 0.4 to 0.6% in water;
   stirring;
   pouring on a smooth support; and
   drying for a period from 2 to 4 days at ambient temperature.

7. The bioreactor of claim 5, having a pellet-shaped bioelectrode, wherein a conductor is glued by means of conductive glue to the surface of the pellet-shaped bioelectrode opposite to the active surface.

8. The bioreactor of claim 5, wherein the membrane comprises a plurality of pores having an average diameter in the range from 1 to 10 nanometers.

9. The bioreactor of claim 5, wherein the membrane comprises a smooth surface facing the pellet-shaped electrode and a rough surface facing outwards.

10. The bioreactor of claim 7, wherein the membrane comprises a plurality of pores having an average diameter in the range from 1 to 10 nanometers.

11. The bioreactor of claim 7, wherein the membrane comprises a smooth surface facing the pellet-shaped electrode and a rough surface facing outwards.

12. The bioreactor of claim 2, wherein the solution comprises from 0.002 to 0.005% in mass per volume of genipin.

13. The bioreactor of claim 2, wherein the solution comprises from 0.001 to 0.005% in mass per volume of caffeic acid.

* * * * *